(12) United States Patent
Olson et al.

(10) Patent No.: US 9,445,812 B2
(45) Date of Patent: *Sep. 20, 2016

(54) CENTER CINCH AND RELEASE OF BUTTRESS MATERIAL

(71) Applicant: Covidien LP, Mansfield, MA (US)

(72) Inventors: Lee Ann Olson, Wallingford, CT (US); Ernest Aranyi, Easton, CT (US); Patrick D. Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 600 days.

This patent is subject to a terminal disclaimer.

(21) Appl. No.: 13/904,652

(22) Filed: May 29, 2013

(65) Prior Publication Data

US 2013/0327807 A1    Dec. 12, 2013

Related U.S. Application Data

(63) Continuation of application No. 13/545,031, filed on Jul. 10, 2012, now Pat. No. 8,453,909, which is a continuation of application No. 13/111,050, filed on May 19, 2011, now Pat. No. 8,235,273, which is a continuation of application No. 12/414,961, filed on Mar. 31, 2009, now Pat. No. 7,967,179.

(51) Int. Cl.
*A61B 17/068* (2006.01)
*A61B 17/072* (2006.01)

(52) U.S. Cl.
CPC ..... *A61B 17/0682* (2013.01); *A61B 17/07207* (2013.01); *A61B 17/07292* (2013.01); *A61B 2017/07214* (2013.01)

(58) Field of Classification Search
CPC .......................... A61B 17/072; A61B 17/068
USPC ......... 227/175.1, 176.1, 180.1; 606/139, 219
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,490,675 A | 1/1970 | Green et al. |
| 3,499,591 A | 3/1970 | Green |

(Continued)

FOREIGN PATENT DOCUMENTS

| | | |
|---|---|---|
| CA | 2 667 434 | 5/2008 |
| CN | 101310680 A | 11/2008 |

(Continued)

OTHER PUBLICATIONS

Extended European Search Report corresponding to EP 08 72 6500.5, completed Feb. 20, 2014 and mailed Mar. 3, 2014; (7 pp).

(Continued)

*Primary Examiner* — Nathaniel Chukwurah

(57) ABSTRACT

A buttressed anvil assembly is provided for use with a surgical stapling instrument. The buttressed anvil assembly generally includes an anvil member having a strip of buttress material attached thereto by a pair of sutures. A tensioning mechanism is provided to secure or tension the buttress material to the anvil member prior to use and allow for release of the buttress material after stapling of tissue. The tensioning mechanism includes a cinch track engageable with one of the pair of sutures.

19 Claims, 5 Drawing Sheets

(56) References Cited

U.S. PATENT DOCUMENTS

| | | |
|---|---|---|
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,476,206 A | 12/1995 | Green et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crows et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 * | 6/2011 | Olson ............ A61B 17/07207 227/175.1 |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |

(56) References Cited

U.S. PATENT DOCUMENTS

| | | |
|---|---|---|
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 * | 8/2012 | Olson .............. A61B 17/07207 227/175.1 |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 * | 6/2013 | Olson .............. A61B 17/07207 227/175.1 |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |

(56) References Cited

U.S. PATENT DOCUMENTS

| | | |
|---|---|---|
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0083723 A1 | 4/2012 | Vitaris et al. |
| 2012/0187179 A1 | 7/2012 | Gleiman |
| 2012/0197272 A1 | 8/2012 | Oray et al. |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Prommersberger |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |

FOREIGN PATENT DOCUMENTS

| | | |
|---|---|---|
| CN | 101332110 A | 12/2008 |
| DE | 1 99 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A2 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 A1 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 | 10/2010 |
| EP | 2 258 282 A2 | 12/2010 |
| EP | 2 292 276 A2 | 3/2011 |
| EP | 2 311 386 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |
| JP | 2000-166933 | 6/2000 |

(56) References Cited

FOREIGN PATENT DOCUMENTS

| | | |
|---|---|---|
| JP | 2002-202213 | 7/2002 |
| JP | 2007-124166 | 5/2007 |
| WO | WO 90/05489 A1 | 5/1990 |
| WO | WO 95/16221 A1 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. Au 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresppondig to EP 12 19 1035.0, completed Jan. 11, 2013 and mailed Jan. 18, 2013; 7 pages.
Extended European Search Report corresppondig to EP 12 19 6904.2, completed Mar. 28, 2013 and mailed Jul. 26, 2013; 8 pages.
Extended European Search Report corresppondig to EP 12 19 8749.9, completed May 21, 2013 and mailed May 31, 2013; 8 pages.
Extended European Search Report corresppondig to EP 07 00 5842.5, completed May 13, 2013 and mailed May 29, 2013; 7 pages.
Extended European Search Report corresppondig to EP 12 19 8776.2, completed May 16, 2013 and mailed May 27, 2013; 8 pages.
Extended European Search Report corresppondig to EP 13 15 6297.7, completed Jun. 4, 2013 and mailed Jun. 13, 2013; 7 pages.
Extended European Search Report corresppondig to EP 13 17 3985.6, completed Aug. 19, 2013 and mailed Aug. 28, 2013; 6 pages.
Extended European Search Report corresppondig to EP 13 17 3986.4, completed Aug. 20, 2013 and mailed Aug. 29, 2013; 7 pages.
European Search Report corresponding to EP 05 02 2585.3, completed Jan. 25, 2006 and mailed Feb. 3, 2006; 4 pages.
European Search Report corresponding to EP 06 00 4598, completed Jun. 22, 2006; 2 pages.
European Search Report corresponding to EP 06 01 6962.0, completed Jan. 3, 2007 and mailed Jan. 11, 2007; 10 pages.
International Search Report corresponding to International Application No. PCT/US2005/036740, completed Feb. 20, 2007 and mailed Mar. 23, 2007; 8 pages.
International Search Report corresponding to International Application No. PCT/US2007/022713, completed Apr. 21, 2008 and mailed May 15, 2008; 1 page.
International Search Report corresponding to International Application No. PCT/US2008/002981, completed Jun. 9, 2008 and mailed Jun. 26, 2008; 2 pages.
European Search Report corresponding to EP 08 25 1779, completed Jul. 14, 2008 and mailed Jul. 23, 2008; 5 pages.
European Search Report corresponding to EP 08 25 1989.3, completed Mar. 11, 2010 and mailed Mar. 24, 2010; 6 pages.
European Search Report corresponding to EP 10 25 0639.1, completed Jun. 17, 2010 and mailed Jun. 28, 2010; 7 pages.
European Search Report corresponding to EP 10 25 0715.9, completed Jun. 30, 2010 and mailed Jul. 20, 2010; 3 pages.
European Search Report corresponding to EP 05 80 4382.9, completed Oct. 5, 2010 and mailed Oct. 12, 2010; 3 pages.
European Search Report corresponding to EP 10 25 1437.9, completed Nov. 22, 2010 and mailed Dec. 16, 2010; 3 pages.
European Search Report corresponding to EP 09 25 2897.5, completed Feb. 7, 2011 and mailed Feb. 15, 2011; 3 pages.
European Search Report corresponding to EP 10 25 0642.5, completed Mar. 25, 2011 and mailed Apr. 4, 2011; 4 pages.
European Search Report corresponding to EP 11 18 8309.6, completed Dec. 15, 2011 and mailed Jan. 12, 2012; 3 pages.
European Search Report corresponding to EP 12 15 2229.6, completed Feb. 23, 2012 and mailed Mar. 1, 2012; 4 pages.

(56) References Cited

OTHER PUBLICATIONS

European Search Report corresponding to EP 12 15 0511.9, completed Apr. 16, 2012 and mailed Apr. 24, 2012; 7 pages.
European Search Report corresponding to EP 12 15 2541.4, completed Apr. 23, 2012 and mailed May 3, 2012; 10 pages.
European Search Report corresponding to EP 12 16 5609.4, completed Jul. 5, 2012 and mailed Jul. 13, 2012; 8 pages.
European Search Report corresponding to EP 12 15 8861.0, completed Jul. 17, 2012 and mailed Jul. 24, 2012; 9 pages.
European Search Report corresponding to EP 12 16 5878.5, completed Jul. 24, 2012 and mailed Aug. 6, 2012; 8 pages.
Extended European Search Report corresponding to EP 12 19 1035.0, completed Jan. 11, 2013 and mailed Jan. 18, 2013; 7 pages.
Extended European Search Report corresponding to EP 12 18 6175.1, completed Jan. 15, 2013 and mailed Jan. 23, 2013; 7 pages.
Extended European Search Report corresponding to EP 12 19 1114.3, completed Jan. 23, 2013 and mailed Jan. 31, 2013; 10 pages.
Extended European Search Report corresponding to EP 12 19 2224.9, completed Mar. 14, 2013 and mailed Mar. 26, 2013; 8 pages.
Extended European Search Report corresponding to EP 12 19 6911.7, completed Apr. 18, 2013 and mailed Apr. 24, 2013; 8 pages.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
Chinese Office Action issued in Chinese Application No. 201410449019.4 dated Mar. 30, 2016.

\* cited by examiner

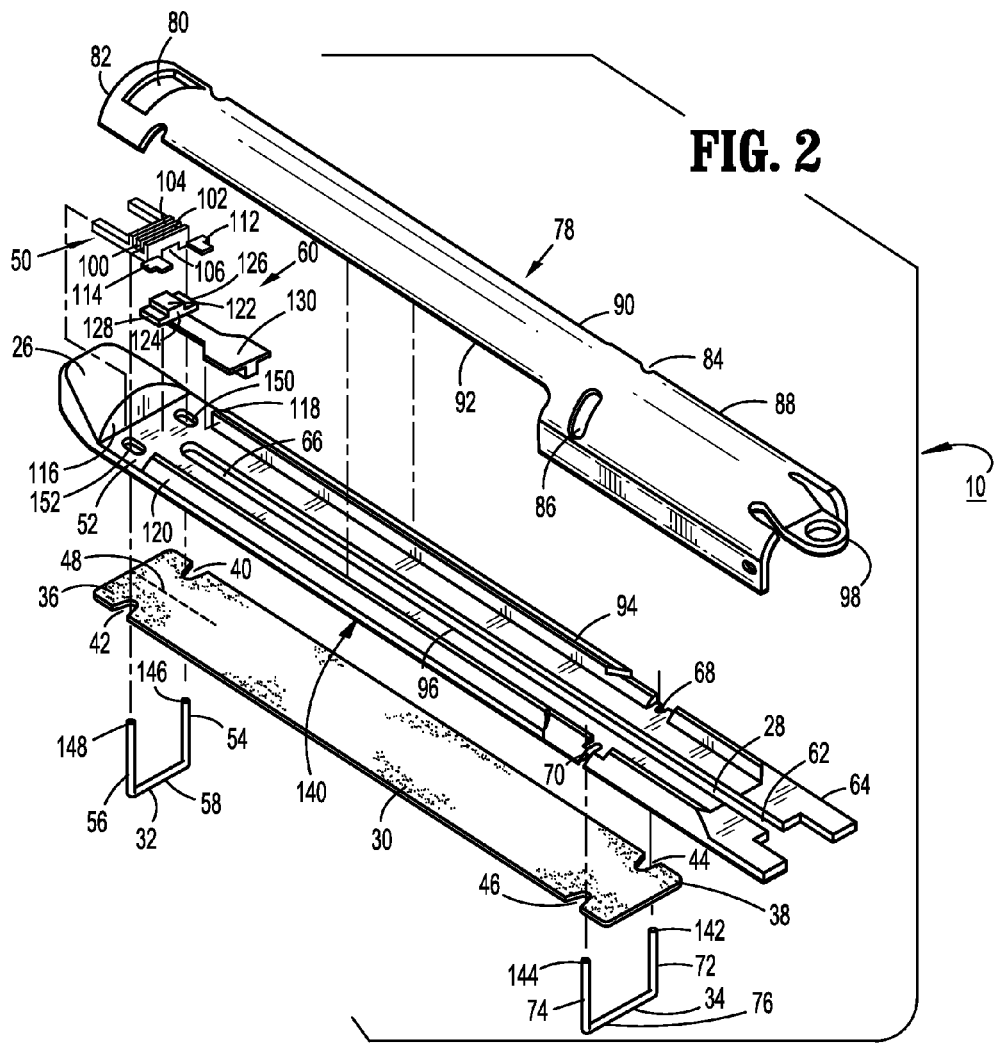
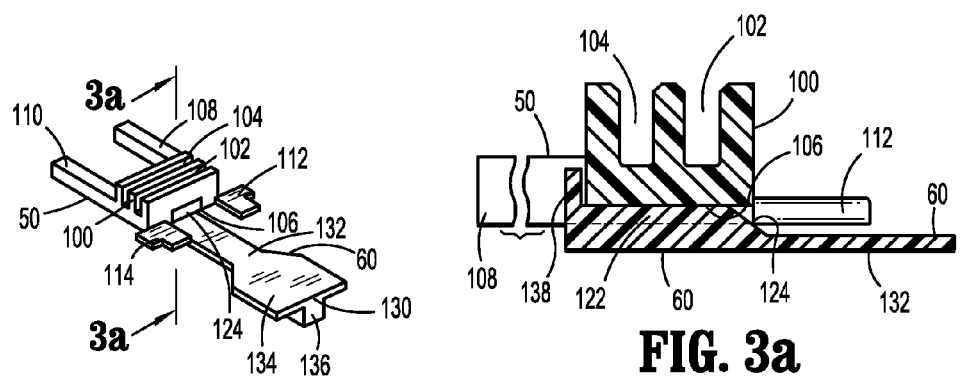

CENTER CINCH AND RELEASE OF BUTTRESS MATERIAL

CROSS-REFERENCE TO RELATED APPLICATIONS

This application is a continuation of U.S. application Ser. No. 13/545,031 filed Jul. 10, 2012, now U.S. Pat. No. 8,453,909, which is a continuation of U.S. application Ser. No. 13/111,050 filed May 19, 2011, now U.S. Pat. No. 8,235,273, which is a continuation of U.S. application Ser. No. 12/414,961 filed Mar. 31, 2009, now U.S. Pat. No. 7,967,179, and the disclosures of each of the above-identified applications are hereby incorporated by reference in their entirety.

BACKGROUND

1. Technical Field

The present disclosure relates to an anvil assembly incorporating a strip of buttress material for use with a surgical stapling instrument. More particularly, the present disclosure relates to a buttress release mechanism for release of the buttress material from the surgical stapling instrument after stapling.

2. Background of Related Art

During various surgical procedures it is often necessary to join two sides of tissue. This is typically accomplished by approximating two edges of the tissues flush against one another and securing them by stapling, suturing, etc. In some instances, the staple or suture line connecting the tissues may tear or tend to pull through the tissues, particularly, where the tissues are diseased and relatively weak. Additionally, during healing, leakage may occur through the staple or suture lines.

In order to alleviate these problems, a strip of material, called "buttress material" is positioned against the tissues prior to stapling or suturing. The buttress material tends to reinforce the staple or suture line as well as tend to prevent leakage prior to healing.

The buttress material may be attached to the surgical instrument being used. For example, the buttress material is often pre-attached to a staple cartridge or anvil assembly of a surgical stapling instrument. The attachment of the buttress material needs be sufficiently secure to allow the surgical instrument to be inserted into the body of a patient as well as allowing the staple cartridge and anvil to be positioned about specific tissues to be stapled. Furthermore, after stapling of the tissues, the buttress material needs to be attached in a manner which allows easy separation of the buttress material from the associated staple cartridge and/or anvil.

Therefore, it is desirable to provide a cartridge or anvil assembly which is capable of easily releasing the buttress material after tissues have been stapled.

SUMMARY

There is disclosed a buttressed anvil assembly for use with a surgical stapling instrument. The buttressed anvil assembly generally includes an anvil having a strip of buttress material positioned adjacent a bottom side of the anvil. Distal and proximal sutures secure the buttress material to the anvil. A tensioning mechanism is provided at a distal end of the anvil assembly. The tensioning mechanism includes a cinch track engageable with the distal suture to hold a distal end of the strip of buttress material against the anvil. The cinch track is movable between a first vertical position tensioning the distal suture against the strip of buttress material to a second vertical position releasing tension on the distal suture to allow release of the strip of buttress material from the anvil.

A release member is provided in the anvil to move the cinch track between the first vertical position and the second vertical position. The release member includes a wedge engageable within a slot formed in the cinch track. A wedge is movable between a first horizontal position maintaining the cinch track in the first vertical position and a second horizontal position allowing the cinch track to move to the second vertical position. A proximal suture may also be provided to secure a proximal end of the strip of buttress material to a proximal end of the anvil.

Specifically, in a particular embodiment, the anvil assembly generally includes an anvil member having a first side and a second side and a length of suture material passing from the first side of the anvil member to the second side of the anvil member. A cinch track is movably mounted on the first side of the anvil member and is engageable with the length of suture. The cinch track is movable between a first vertical position tensioning the length of suture and a second vertical position releasing tension on the length of suture. A release member is movably mounted on the first side of the anvil member and is movable relative to the cinch track between a first horizontal position and a second horizontal position. The release member maintains the cinch track in the first vertical position when the release member is in the first horizontal position and allows the cinch track to move to the second vertical position when the release member is in the second horizontal position.

The anvil assembly additionally includes a strip of buttress material positioned adjacent the second side of the anvil member. The length of suture includes a backspan and first and second suture sides extending from the backspan. The backspan is engageable with the strip of buttress material to maintain the strip of buttress material adjacent the second side of the anvil member when the cinch track is in the first vertical position.

The anvil member includes first and second holes extending between the first and second sides of the anvil member. The first side of the length of suture material extends through the first hole and the second side of the suture material extends through the second hole. The cinch track includes a first track and the first suture side is secured in the first track. The cinch track also includes a second track and the second suture side is secured in the second track.

The release member includes a wedge and the cinch track includes a slot such that the cinch track is in the first vertical position when the wedge is positioned within the slot and is in the second vertical position when the wedge is out of the slot. The anvil member includes a longitudinally extending slot and the release member includes a guide rib movable within the longitudinally extending slot.

The strip of buttress material includes a perforation line adjacent a distal end of the buttress material to allow separation of the buttress material distally of the anvil slot. The strip of buttress material includes first and second cutouts to accommodate passage of the first and second sides of the length of suture material.

The anvil assembly additionally includes a proximal length of suture material for securing a proximal end of the strip of buttress material to the anvil member. The proximal length of suture material includes a backspan and first and second sides extending from the backspan. The backspan secures a proximal end of the strip of buttress material to the second side of the anvil member. The anvil member includes a pair of slots adjacent the proximal end of the anvil member. The pair of slots is dimensioned to frictionally secure the first and second sides of the proximal length of suture material. The strip of buttress material includes first and second cutouts formed adjacent the proximal end of the strip of buttress material for passage of the first and second sides of the proximal length of suture material.

The anvil assembly further includes a cover affixed to the anvil member. The cover including a distal window providing visualization of the cinch track and a pair of proximal windows providing visualization of the first and second sides of the proximal length of suture material secured within the first and second slots formed in the anvil member.

DESCRIPTION OF THE DRAWINGS

An embodiment of the presently disclosed buttressed anvil assembly is disclosed herein with reference to the drawings, wherein:

FIG. 2 is a perspective view, with parts separated, of the buttressed anvil assembly incorporating a strip of buttress material;

FIG. 3 is a perspective view of a cinch track and release bar of the buttressed anvil assembly;

FIG. 3a is a side view, partially shown in section, taken along the line 3a-3a of FIG. 3;

DETAILED DESCRIPTION OF EMBODIMENTS

An embodiment of the presently disclosed buttressed anvil assembly will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
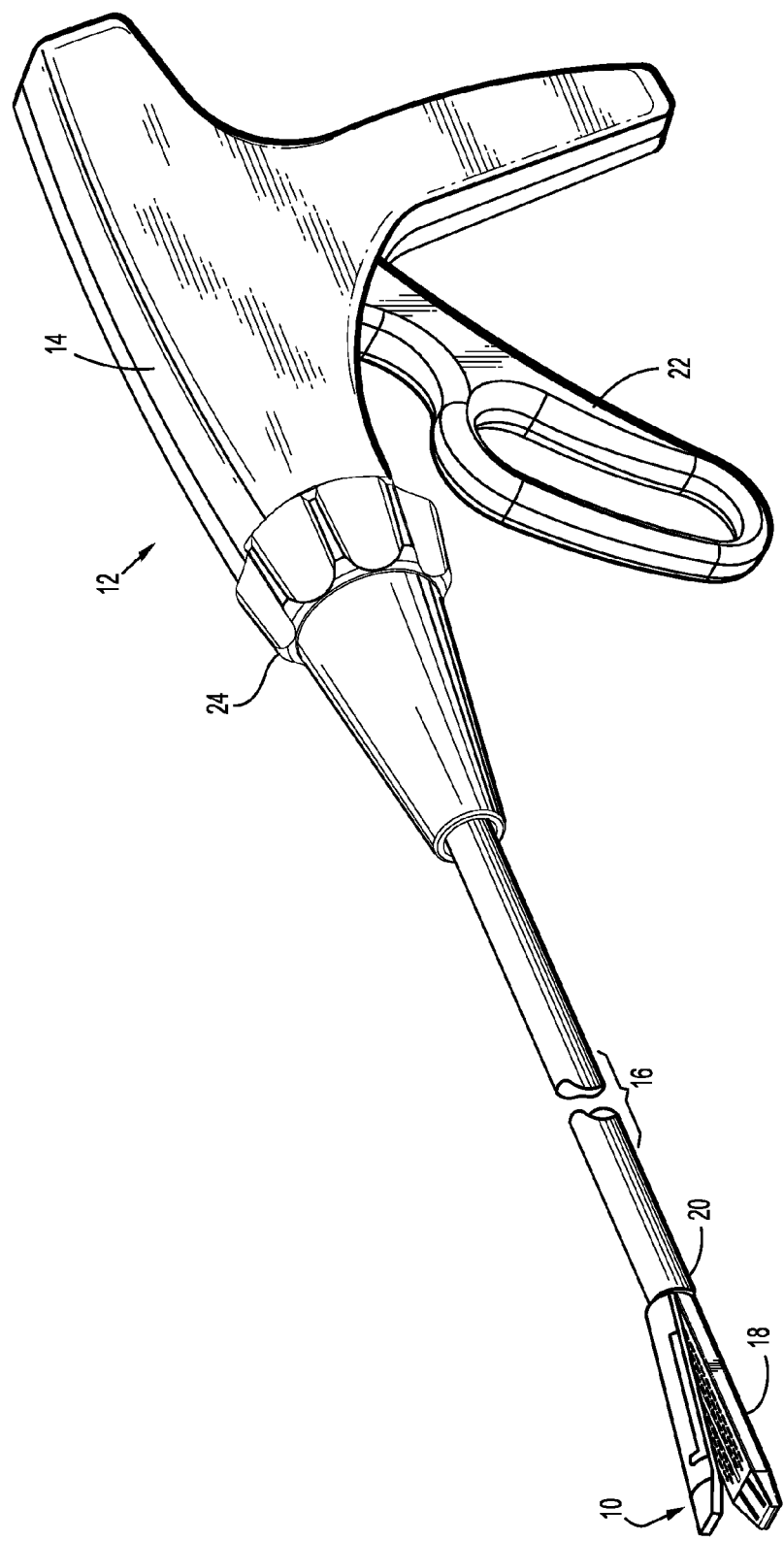
FIG. 1 is a perspective view of a surgical stapling instrument incorporating a buttressed anvil assembly.

Referring to FIG. 1, there is disclosed a buttressed anvil assembly or anvil assembly 10 for use with a surgical stapling instrument 12. As used herein, "buttress" includes pledgets, staple line reinforcement material, gaskets, and other materials used in conjunction with surgical instruments for joining tissue. Surgical stapling instrument 12 is a type well known in the art and is embodied in U.S. Pat. Nos. 5,762,256; 5,782,396; and 6,032,849, the contents of which are expressly incorporated herein by reference.

Surgical stapling instrument 12 generally includes a pistol grip body portion 14 having an elongate tubular member 16 extending distally from body portion 14. A staple cartridge 18 is mounted on a distal end 20 of elongate tubular member 16. Anvil assembly 10 is movably mounted on a distal end 20 of elongate tubular member 16 and is movable between an open position spaced apart from staple cartridge 18 to a closed position wherein anvil assembly 10 is in close cooperative alignment with staple cartridge 18.

In order to move anvil assembly 10 between the open and closed positions, surgical stapling instrument 12 includes a trigger 22 pivotally mounted to body portion 14. Trigger 22 controls the linear movement of an actuation shaft (not shown) which is mounted within the elongated tubular member 16. The actuation shaft operates to move a drive beam (not shown) distally to initially move the anvil assembly 10 between the open and closed positions. The drive beam also acts to move an actuation sled (not shown) distally through the staple cartridge 18 to eject staples. The drive beam includes a knife blade to cut tissue as the drive beam translates through the staple cartridge 18. A rotation knob 24 is provided to orient anvil assembly 10 and staple cartridge 18 relative to the tissue being stapled.

Although surgical stapling instrument 12 is shown with a single trigger 22 which accomplishes both jaw closure and firing of staples, it is further contemplated that the present buttress release mechanism can also be used with surgical stapling instruments of the type which utilize a clamping mechanism to close the jaws which is separate from the firing mechanism. See, for example, U.S. Pat. No. 5,476, 206, the contents of which are expressly incorporated herein by reference.

Referring now to FIG. 2, anvil assembly 10 generally includes an anvil member 26, having a knife slot 28 extending longitudinally partially through anvil member 26, and a length or strip of buttress material 30. Strip of buttress material 30 is secured to anvil member 26 by a first or distal suture 32 and a second or proximal suture 34. Distal and proximal sutures 32 and 34 secure respective distal and proximal ends 36 and 38 of buttress material 30 to anvil member 26 in a manner described in more detail hereinbelow.

Buttress material 30 further includes a pair of distal cutouts 40 and 42 formed adjacent distal end 36 of buttress material 30. Distal cutouts 40 and 42 are provided to accommodate passage of distal suture 32 to secure buttress material 30 to anvil member 26 and prevent any distal movement of buttress material 30 relative to anvil member 26. Similarly, a pair of proximal cutouts 44 and 46 is formed adjacent proximal end 38 of buttress material 30. Proximal cutouts 44 and 46 are provided to receive proximal suture 34 to secure proximal end 38 of buttress material 30 to anvil member 26 and prevent any longitudinal motion of buttress material 30. It should be noted that, during stapling and cutting of tissue, distal end 36 of buttress material 30 is distal of knife slot 28 and thus is not cut. A perforation line 48 may be formed in distal end 36 to facilitate separation of buttress material 30 into two halves after tissue has been stapled and cut.

In order to maintain tension of distal suture 32 against buttress material 30 prior to the cutting of tissue and to allow for the release of tension of distal suture 32 against buttress material 30, anvil assembly 10 further includes a cinch track 50 which is positioned within a distal end 52 of anvil member 26. Cinch track 50 is movable between a first vertical position tensioning distal suture 32 against buttress material 30 and a second vertical position releasing tension of distal suture 32 against buttress material 30. Cinch track 50 is provided to securely engage first and second sides 54 and 56 of first suture 32. The suture can be preformed in a shape defining the first side 54, second side 56, and backspan 58, or can comprise an ordinary suture that is wrapped around the anvil so as to defining the first side 54, second side 56, and backspan 58. The backspan 58 of first suture 32 lies against the distal end 36 of buttress material 30 against anvil member 26.

In order to move cinch track 50 between the first and second vertical positions, a release member 60 is provided and is longitudinally or horizontally movable within anvil member 26 in a manner described in more detail hereinbelow. The release member 60 may be formed as a bar, rod, cable or other member.

As shown, knife slot 28 has a proximal end 62 which is open at proximal end 64 of anvil member 26. A distal end 66 of knife slot 28 terminates proximally of distal end 52 of anvil member 26. As noted herein above, buttress material 30 includes a perforation line 48 to facilitate separation of distal end 36 of buttress material 30 as it is located distally of distal end 66 of knife slot 28.

In order to secure a proximal end 38 of buttress material 30 against anvil member 26, anvil member 26 is provided with a pair of slots 68 and 70 which are configured to securely receive first and second sides 72 and 74 of proximal suture 34. The proximal suture can be preformed in a shape or comprise an ordinary suture wrapped around the anvil member so as to define first side 72, second side 74 and backspan 76. The backspan 76 of proximal suture 34 engages proximal end 38 of buttress material 30 to secure proximal end 38 against anvil member 26.

Anvil assembly 10 additionally includes an anvil cover 78 having a distal cinch window 80 formed in a distal end 82 of anvil cover 78. Distal cinch window 80 is provided to allow the surgeon to visually confirm the engagement of distal suture 32 with cinch track 50. A pair of proximal cinch windows 84 and 86 are provided adjacent proximal end 88 of anvil cover 78 and serve to allow the surgeon to visually confirm the engagement of proximal suture 34, specifically the engagement of first and second sides 72 and 74, with slots 68 and 70 formed in proximal end 64 of anvil member 26.

Anvil cover 78 includes longitudinally extending side cuts 90 and 92 which are configured to engage side walls 94 and 96, formed in anvil member 26, in friction fit fashion to secure anvil cover 78 to anvil member 26. Alternatively, the anvil cover may be attached using welding, adhesives or other means. Mounting structure 98 is provided on proximal end 88 to facilitate attachment of anvil assembly 10 to distal end 20 of elongate tubular member 16 (FIG. 1).

The cinch track generally includes a body portion defining one or more tracks. Referring now to FIGS. 3 and 3a, cinch track 50 has a body portion 100 with first and second tracks 102 and 104. First and second tracks 102 and 104 are dimensioned to pinch or cinch first and second sides 54 and 56, respectively, of suture 32 to secure suture 32 to cinch track 50. Body portion 100 additionally includes a center slot 106 for receipt of release member 60 in a matter discussed in more detail hereinbelow.

As noted herein above, cinch track 50 is positioned within distal end 52 of anvil member 26 and is movable between first and second vertical positions relative to anvil member 26. As specifically shown in FIG. 3, a pair of distal arms 108 and 110 extend distally from body portion 100 while proximal tabs 112 and 114 extend proximally from body portion 100. Distal arms 108 and 110 are positioned against a proximal face 116 formed in distal end 52 of anvil member 26 (FIG. 2). Likewise, proximal tab 112 and proximal tab 114 are configured to loosely engage distal ends 118 and 120 of side walls 94 and 96 formed in anvil member 26 allowing cinch track 50 to move vertically within distal end 52 of anvil member 26 (FIG. 2).

Referring back for the moment to FIG. 2, as noted herein above, release member 60 is provided to move cinch track 50 between the first and second vertical positions. Release member 60 includes a distal wedge 122 which is configured to ride within center slot 106 of cinch track 50 to move cinch track 50 between the first and second vertical positions. A sloped face 124 extends proximally from distal wedge 122. Sides 126 and 128 of distal wedge 122 facilitate guiding distal wedge 122 against cinch track 50. In the embodiment of FIG. 3a, the bottom surface of the cinch track 50 is generally horizontal. However, in other embodiments, one or more surfaces can be shaped to cooperate with the sloped face 124, such as a cam surface, and may correspond to the shape of the sloped face 124.

Referring now to FIG. 3, release member 60 further includes a guide bar 130 extending proximally from distal wedge 122. Guide bar 130 includes a central portion 132 and a proximally extending flanged portion 134. Flanged portion 134 helps align release bar 60 within side walls 94 and 96 of anvil member 26. As shown, a guide rib 136 extends downwardly from guide bar 130 and is configured to ride within knife slot 28 such that release member 60 is movable in a longitudinal or horizontal direction relative to cinch track 50.

With specific reference to FIG. 3a, it can be seen that wedge 122 of release member 60 is configured to move body portion 100 of cinch track 50 vertically. Sloped face 124 of release member 60 facilitates assembly of anvil assembly 10, and specifically, allows for reset of release member 60 to pre-fire and assembly condition. A base stop 138 is provided on distal wedge 122 of release member 62 to prevent pulling wedge 122 completely through center slot 106 of cinch track 50 during assembly.

Referring now to FIGS. 2-7, and initially with regard to FIG. 2, the assembly of a strip of buttress material 30 to anvil member 26 will now be described. Proximal end 38 of strip of buttress material 30 is secured to proximal end 64 of anvil member 26. Specifically, proximal end 38 is positioned against an underside 140 of anvil member 26. Proximal suture 34 is manipulated such that first and second free ends 142 and 144 of first and second sides 72 and 74 pass through cutouts 44 and 46 to bring backspan 76 of proximal suture 34 into engagement with proximal end 38 of strip of buttress material 30.

Thereafter, first and second sides 72 and 74 are positioned within slots 68 and 70 in anvil member 26. During positioning, first and second side 72 and 74 are tensioned so as to secure proximal end 38 of strip of suture material 30 against underside 140 of anvil member 26. As noted herein above, slots 68 and 70 are dimensioned so as to pinch or cinch first and second sides 72 and 74. Once strip of suture material 30 has been secured, the excess material of first and second side 72 and 74 extending beyond slots 68 and 70 may be trimmed off through the cover. It should be noted that, since proximal end 38 of strip of suture material 30 stretches across knife slot 28, there is no need to release the tension on proximal suture 34 as it will be cut by a knife blade (not shown) during the stapling procedure.

With reference to FIGS. 2-7, the assembly of distal end 36 of strip of suture material 30 to anvil member 26 will now be described. Initially, with respect to FIGS. 3 and 3a, release member 60 is in a first or proximal most position. Cinch track 50 is in a first or vertically highest most position due to the passage and engagement of wedge 122 of release member 60 within slot 106 formed in body portion 100 of cinch track 50.

With reference to FIG. 2, distal end 36 of strip of buttress material 30 is positioned flush against underside 140 of anvil member 26. Distal suture 32 is manipulated such that free ends 146 and 148 of first and second sides 54 and 56, respectively, passed through cutouts 40 and 42 formed in distal end 36 of strip of buttress material 30. As shown, distal end 52 of anvil member 26 is provided with a pair of spaced apart holes 150 and 152. Free ends 146 and 148 of distal suture 32 are passed through holes 150 and 152 such that first and second sides 54 and 56 are aligned alongside first and second tracks 102 and 104 of cinch track 50. Vertical tension is applied to free ends 146 and 148 to secure distal end 36 of strip a buttress material 30 against underside 140 of anvil member 26.

Figure 6:
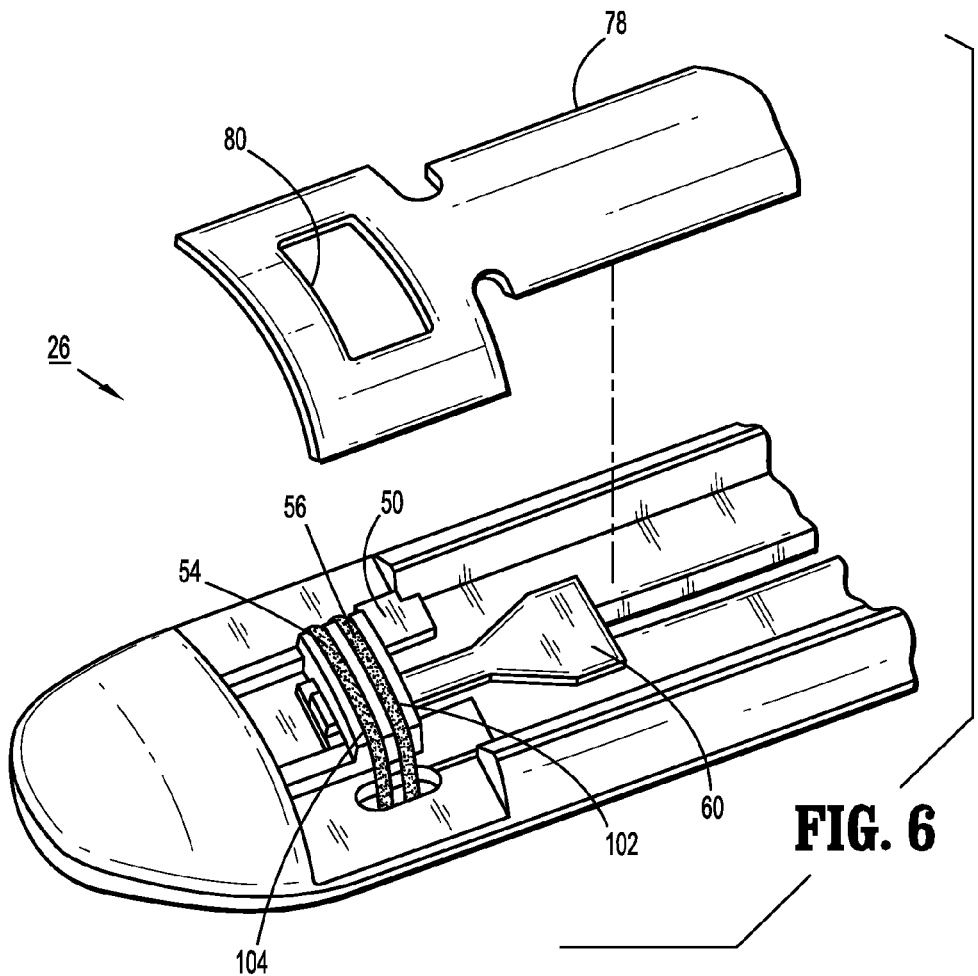
FIG. 6 is a perspective view similar to FIG. 4 with an anvil cover removed.
Figure 7:
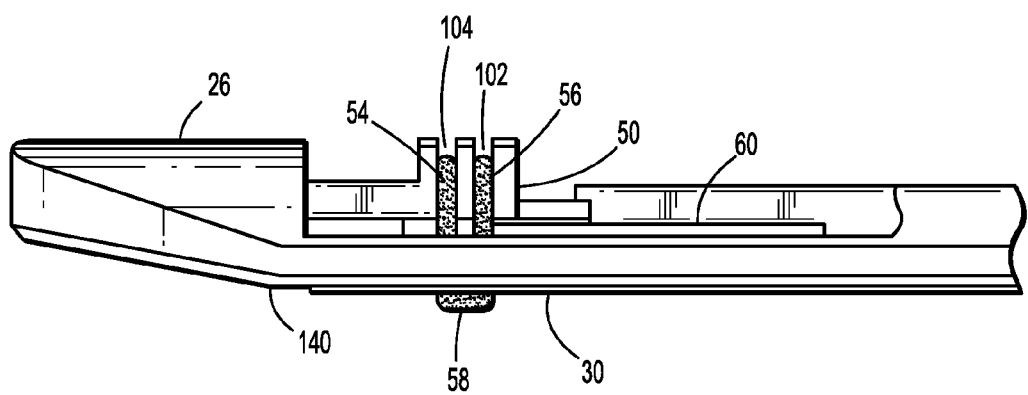
FIG. 7 is a side view of the distal end of the buttressed anvil assembly with the anvil cover removed.

First and second sides 54 and 56 are then manipulated such that first side 54 passes within second track 104 and second side 56 passes within first track 102 (see also FIGS. 6 and 7). As noted herein above, first and second tracks 102 and 104 are dimensioned so as to pinch or cinch a suture positioned therein. Thereafter, excess material of first and second sides 54 and 56 of distal suture 32 may be trimmed off. Finally, cover 78 is affixed to anvil member 26 in the manner described herein above.

Figure 4:
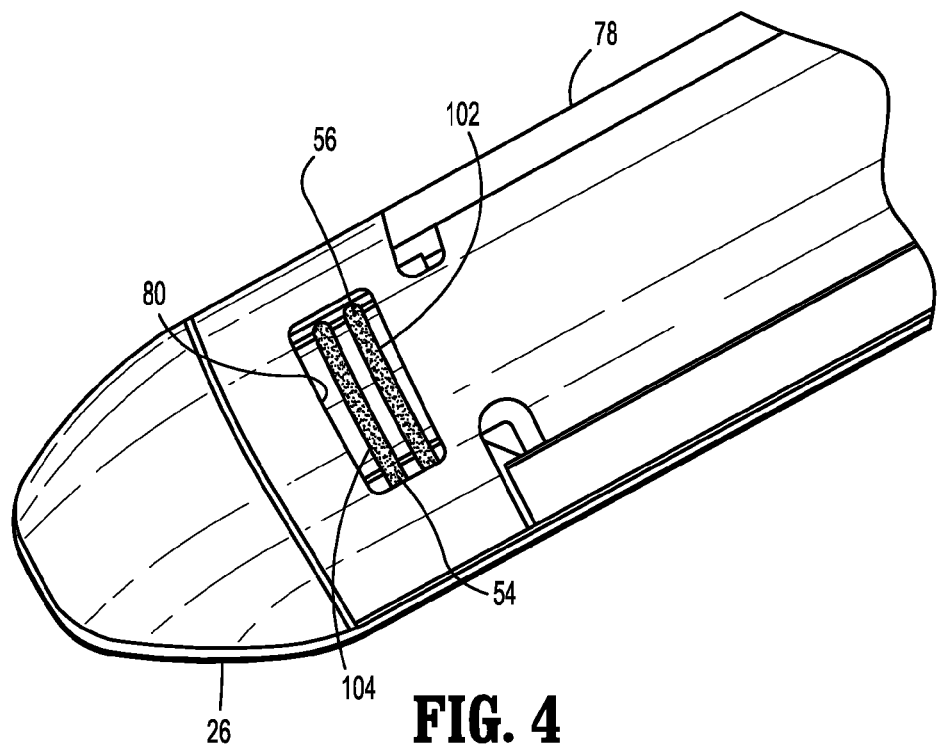
FIG. 4 is a perspective view of the distal end of the buttressed anvil assembly taken from the top.
Figure 5:
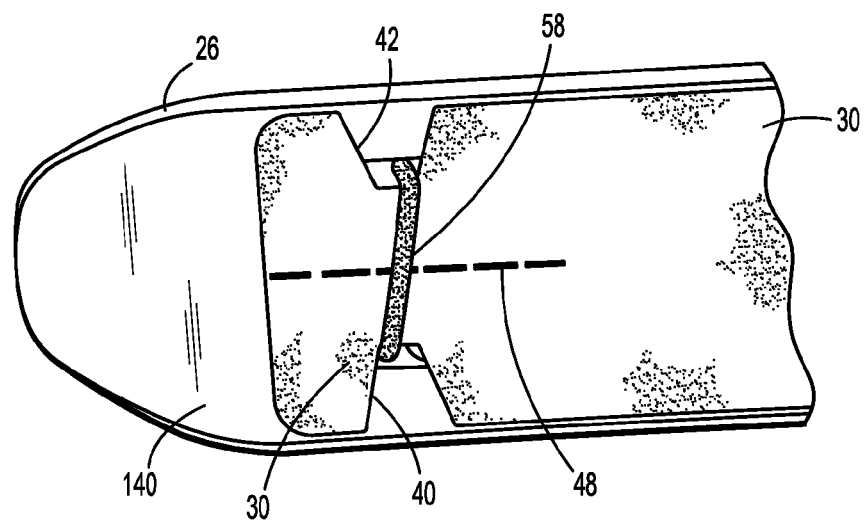
FIG. 5 is a perspective view of the distal end of the buttressed anvil assembly taken from the bottom.

With reference to FIGS. 4 and 5, in the assembled condition, first and second sides 54 and 56 of distal suture 32 are visible through distal cinch window 80 in cover 78 for verification (FIG. 4). Likewise, backspan 58 of distal suture 32 can be confirmed as extending across perforation line 48 and strip of suture material 30 (FIG. 5).

Referring now to FIGS. 1 and 6-10, the use of anvil assembly 10 will now be described. With reference to FIGS. 6 and 7, and as described herein above, in the initial position release bar 60 is in a first or proximal most position maintaining cinch track 50 in a first or vertically highest position relative to anvil member 26 thereby maintaining tension of backspan 58 of distal suture 32 against distal end 36 of strip of buttress material 30.

In use, with reference to FIG. 1, surgical stapling instrument 12 is manipulated such that anvil assembly 10 and staple cartridge 18 are positioned about the tissue (not shown) to be stapled. Once surgical stapling 12 has been properly positioned, trigger 22 is actuated to move anvil assembly 10 to the closed position about tissue relative to staple cartridge 18. While not specifically shown, anvil pockets are provided on anvil member 26 to clinch staples ejected out of staple cartridge 18 through the subject tissue and through strip of buttress material 30.

Figure 8:
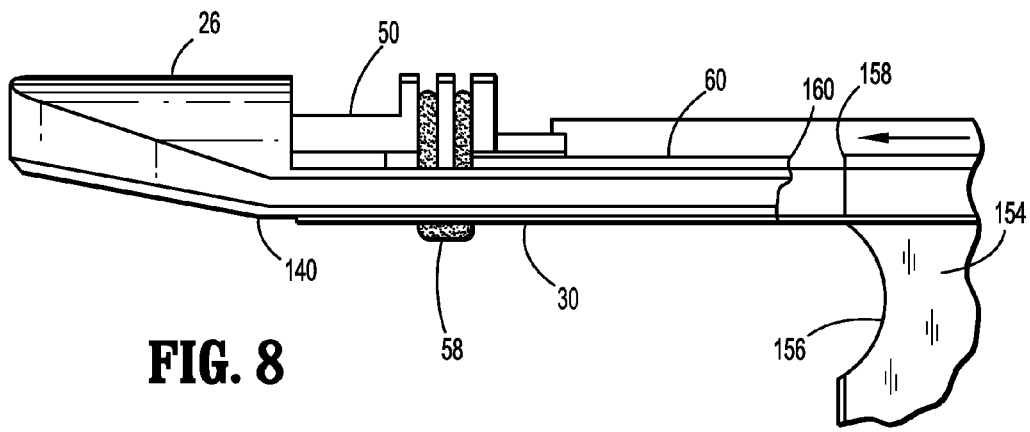
FIG. 8 is a side view similar to FIG. 7 during the initial advancement of a knife bar toward the release bar.

Referring back for the moment to FIG. 2, and as noted herein above, backspan 76 of proximal suture 34 extends across knife slot 28. Referring now to FIG. 8, a knife bar 154 is associated with surgical stapling instrument 12 to cut through staple lines formed in the tissue by staple cartridge 18 and anvil assembly 10. As knife bar 154 passes distally through knife slot 28 a blade 156 of knife bar 154 cuts through proximal end 38 of strip of buttress material 30 and severs backspan 76 a proximal suture 34. Continued advancement of knife bar 154 distally through slot 28, causes blade 156 to continue to cut through strip of buttress material 30.

Figure 9:
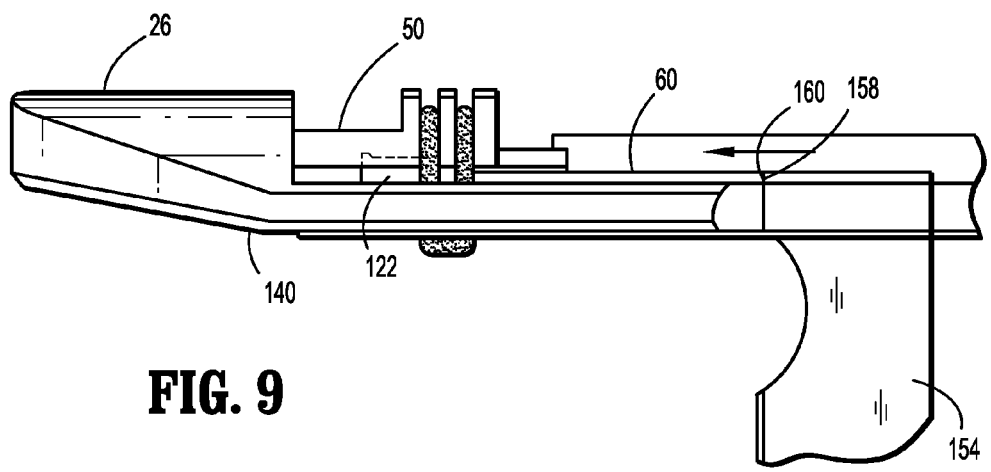
FIG. 9 is a side view similar to FIG. 8 illustrating the engagement of the knife bar with the release bar.

With continued reference to FIG. 8, as knife bar 154 advances distally through anvil member 26, a distal top edge 158 of knife bar 154 approaches a proximal edge 160 of release member 60. As best shown in FIG. 9, as distal edge 158 of knife bar 154 moves distally it engages proximal edge 160 of release member 60, knife bar 154 begins to drive release member 60 distally such that distal wedge 122 of release member 60 is driven distally through slot 106 (FIGS. 2 and 3) formed in cinch track 50.

Figure 10:
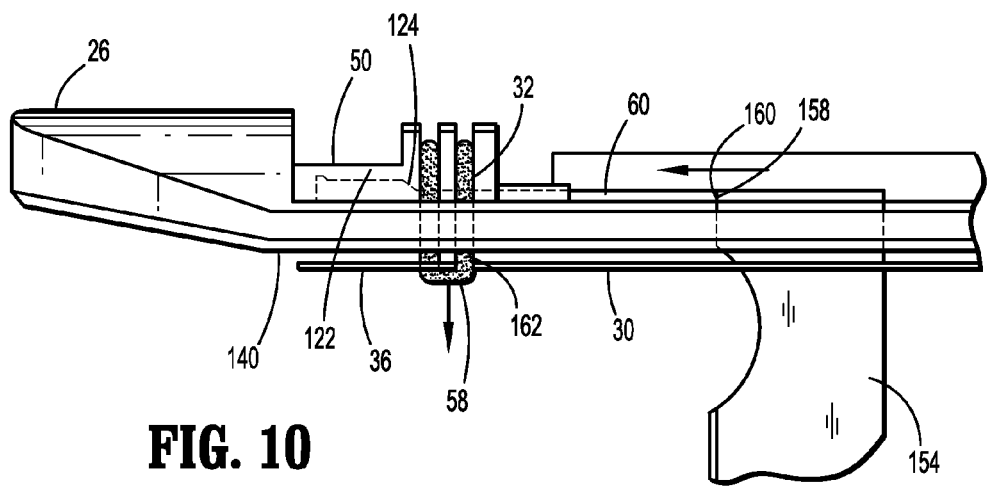
FIG. 10 is a side view similar to FIG. 8 illustrating the knife bar advancing the release bar through the cinch track to release tension on the strip of buttress material.

With specific reference to FIG. 10, as release member 60 is driven to a second or distal most position by a knife bar 54, sloped face 124 of distal wedge 122 clears slot 106 allowing cinch track 50 to drop down to a second or vertically lowest most position relative to anvil member 26. As shown, when cinch track 50 is in the second or vertically lowest position, tension is released on distal suture 32 such that backspan 58 of distal suture 32 drops a substantial distance below underside 140 of anvil member 26. This creates an opening or gap 162 between backspan 58 of distal suture 32 and underside 140 of anvil member 26.

Once knife bar 154 has reached a distal most position, pressure on trigger 22 may be released allowing anvil member 10 to move to the open position relative to staple cartridge 18 (FIG. 1). As anvil assembly 10 is moved to the open position, distal end 36 of strip of buttress material 30, being stapled the tissue, pulls free through gap 162 allowing distal end 36 to separate from anvil member 26. As noted herein above, and as shown in FIG. 2, perforation line 48 is formed in distal end 36 of strip of buttress material 30 allowing strip of buttress material 30 to separate into halves generally along the cut line formed by knife blade 156 through strip of buttress material 30. In this manner, anvil assembly 10 allows for simple and easy assembly of a strip of buttress material 30 to with anvil member 26 and, more importantly, allows for easy release of distal end 36 of a strip of buttress material 30 from anvil member 26.

It will be understood that various modifications may be made to the embodiments disclosed herein. For example, the release member could be arranged to be pulled proximally to change the position of the cinch track and release the suture and buttress. In other embodiments, the proximally pulled release member, or the release member 60 discussed above, may be connected to a separate actuator on the handle of the surgical instrument, for engagement by the user of the instrument. In another example, the disclosed cinch track may have more or fewer tracks to accommodate more or fewer wraps of a length of suture material. Further, the disclosed tensioning mechanisms, including the suture track and the release bar, may be adapted to be incorporated in a staple cartridge and to function with driving bars in the staple cartridge. Additionally, the disclosed methods and structure for releasing tension on a suture maintaining a strip of buttress material may find use in other forms of surgical staplers such as, for example, circular staplers, etc. In further embodiments, a release member pushes cinch track down vertically to release the tension on the suture and release the buttress. Therefore, the above description should not be construed as limiting, but merely as exemplifications of particular embodiments. Those skilled in the art will envision other modifications within the scope and spirit of the claims appended hereto.

The invention claimed is:

1. An anvil assembly comprising:
   an anvil member;
   a length of suture material;
   a strip of buttress material secured to the anvil member with the suture material;
   a track movably mounted to the anvil member and engageable with the length of suture, the track movable between a first position tensioning the length of suture and a second position releasing tension on the length of suture; and a release member movably mounted to the anvil member and movable relative to the track to move the track to the second position.

2. The anvil assembly as recited in claim 1, wherein the length of suture includes a backspan and first and second suture sides extending from the backspan, the backspan engageable with the strip of buttress material to maintain the strip of buttress material adjacent the anvil member when the track is in the first position.

3. The anvil assembly as recited in claim 2, wherein the track includes a first track and the first suture side is secured in the first track.

4. The anvil assembly as recited in claim 3, wherein the track includes a second track and a second suture side is secured in the second track.

5. The anvil assembly as recited in claim 3, further comprising a cover affixed to the anvil member, the cover including a distal window providing visualization of the track.

6. The anvil assembly as recited in claim 2, wherein the release member includes a wedge and the track includes a slot such that when the track is in the first position the wedge is positioned within the slot, and when the wedge is out of the slot the track is in the second position.

7. The anvil assembly as recited in claim 2, wherein the anvil member includes first and second holes extending between sides of the anvil member, wherein the first side of the length of suture material extends through the first hole and the second side of the length of suture material extends through the second hole.

8. The anvil assembly as recited in claim 2, wherein the strip of buttress material includes first and second cutouts to accommodate passage of the first and second sides of the length of suture material.

9. The anvil assembly as recited in claim 2, further comprising a proximal length of suture material for securing a proximal end of the strip of buttress material to the anvil member.

10. The anvil assembly as recited in claim 9, wherein the proximal length of suture material includes a backspan and first and second sides extending from the backspan, the backspan securing the strip of buttress material to the anvil member.

11. The anvil assembly as recited in claim 10, wherein the anvil member includes a pair of slots adjacent a proximal end of the anvil member, the pair of slots being dimensioned to frictionally secure the first and second sides of the proximal length of suture material.

12. The anvil assembly as recited in claim 11, further comprising a cover affixed to the anvil member, the cover including a pair of proximal windows, the proximal windows providing visualization of the first and second sides of the proximal length of suture material secured within the first and second slots formed in the anvil member.

13. The anvil assembly as recited in claim 10, wherein the strip of buttress material includes first and second cutouts formed adjacent the proximal end of the strip of buttress material for passage of the first and second sides of the proximal length of suture material.

14. The anvil assembly as recited in claim 1, wherein the anvil member includes a longitudinally extending slot and the release member includes a guide rib movable within the longitudinally extending slot.

15. The anvil assembly as recited in claim 1, wherein the strip of buttress material includes a perforation line to facilitate separation of the strip of buttress material after firing the anvil assembly.

16. The anvil assembly as recited in claim 1, wherein the release member moves between a first horizontal position and a second horizontal position, wherein the release member maintains the track in the first vertical position when the release member is in the first horizontal position and allows the track to move to the second vertical position when the release member is in the second horizontal position.

17. A surgical stapling apparatus, comprising:
an anvil assembly comprising:
an anvil member having a first side and a second side;
a length of suture material passing from the first side of the anvil member to the second side of the anvil member;
a track movably mounted on the first side of the anvil member and engageable with the length of suture, the track movable between a first vertical position tensioning the length of suture and a second vertical position releasing tension on the length of suture; and
a release member movably mounted on the first side of the anvil member and movable relative to the track to move the track to the second vertical position.

18. The surgical stapling apparatus as recited in claim 17, further comprising a strip of buttress material positioned adjacent the anvil member.

19. A surgical stapling apparatus, comprising:
a knife assembly including a knife blade; and
an anvil assembly comprising:
an anvil member including a knife slot, wherein the knife blade is distally movable through the knife slot;
a proximal suture and a distal suture, each suture having a first side, a second side, and a backspan extending between the first and second sides;
a strip of buttress material having a distal end and a proximal end, the strip of buttress material being secured to the anvil member by the distal suture and the proximal suture, wherein the distal suture secures the distal end of the strip of buttress material and the proximal suture secures the proximal end of the strip of buttress material, and wherein the backspan of the proximal suture extends across the knife slot such that the knife blade cuts the proximal end of the strip of buttress material and severs the backspan of the proximal suture as the knife blade moves distally through the knife slot;
a track movably mounted to the anvil member and engageable with the distal suture, the track movable between a first position tensioning the distal suture and a second position releasing tension on distal suture; and
a release member movably mounted to the anvil member and movable relative to the track to move the track to the second position.

* * * * *